United States Patent [19]

Blytas et al.

[11] Patent Number: 4,810,340
[45] Date of Patent: Mar. 7, 1989

[54] PROCESS FOR RECOVERING ORGANIC VALUES FROM AQUEOUS SOLUTIONS CONTAINING BOTH ORGANIC VALUES AND SCALE-FORMING IONS

[75] Inventors: George C. Blytas; Zaida Diaz, both of Houston, Tex.

[73] Assignee: Shell Oil Company, Houston, Tex.

[21] Appl. No.: 21,823

[22] Filed: Mar. 3, 1987

[30] Foreign Application Priority Data

Nov. 13, 1986 [GB] United Kingdom ............... 8627130

[51] Int. Cl.$^4$ ...................... B01D 13/02; B01D 57/02; C02F 1/46
[52] U.S. Cl. ................................ 204/182.4; 204/151; 204/131; 203/14; 203/18
[58] Field of Search ............... 204/301, 130, 131, 149, 204/151, 182.4, 182.3, 182.5, 182.6; 203/14, 15, 16, 17, 18, DIG. 16

[56] References Cited

U.S. PATENT DOCUMENTS

| 4,395,337 | 7/1983 | Ciepiela | 210/703 |
| 4,427,507 | 1/1984 | van Aken et al. | 204/182.4 |
| 4,676,908 | 6/1987 | Ciepiela et al. | 210/669 |

*Primary Examiner*—John F. Niebling
*Assistant Examiner*—John S. Starsiak, Jr.
*Attorney, Agent, or Firm*—Ronald R. Reper

[57] ABSTRACT

An improved process for recovering organic values from aqueous solutions containing scale-forming ions by electrodialysis and fractionation-distillation, wherein an aqueous substantially free of organics is introduced into the concentrate side of the electrodialysis membranes to substantially reduce or avoid scaling on said membranes.

8 Claims, No Drawings

PROCESS FOR RECOVERING ORGANIC VALUES FROM AQUEOUS SOLUTIONS CONTAINING BOTH ORGANIC VALUES AND SCALE-FORMING IONS

BACKGROUND OF THE INVENTION

The present invention relates to a process for the recovery of organic values from aqueous solutions containing both organic values and scale-forming ions, and more particularly to a process for recovery of polyhydric organic compounds from spent dehydrating agents employed for drying water-containing $CO_2$. Procedures for drying $CO_2$, particularly at supercritical or near critical conditions, with electrolytes and/or polyhydric organic compounds such as calcium chloride, polyglycols such as triethlyene glycol, and glycerine are disclosed e.g. in U.S. Pat. Nos. 4,478,612; 4,492,592; 4,492,593; and 4,500,333 (all incorporated by reference).

The recovery of organic values from aqueous solutions containing electrolytes has often been realized commercially by the use of evaporative processing, in which the water is first evaporated, then the desired organic substances are evaporated and recovered. In this procedure the electrolytes concentrate at in the bottom of the evaporation equipment, and when scale-forming electrolytes are present the evaporative process can be hampered by scale formation and resulting loss of heat exchanging efficiency at the surfaces of the associated heat exchanging units.

As the heat transfer becomes ineffective due to fouling, the skin temperatures in the heat exchanger must be increased, which may result in localized "hot spots" and increased propensity of the organic molecules to decompose. The present invention circumvents this problem by first electrodialyzing the feed to remove the electrolytes under conditions Which will not cause precipitation of scale which might otherwise occur in the electrodialysis unit.

The precipitation of scale can be particularly serious at higher pH values during electrodialysis, e.g. in the region above about 9 pH. Thus, the presence of bicarbonate ions can be deleterious, in that at high pH carbonate ions would form which would lead to precipitation of e.g. calcium as the carbonate. Further it has been found that the aqueous solutions resulting from the drying of subterranean $CO_2$ always contain bicarbonate ion and often contain in addition to calcium, other divalent metal ions such as magnesium and barium, and sulfate ions as well. The formation of e.g. calcium sulfate scale is particularly troublesome as it is difficult to remove from the surface of heat exchange equipment, even after acid washing. In an electrodialysis unit the scale formation can be a serious problem in the area close to the anion exchange membranes. During normal operation, localized conditions in these regions can result in pH values which are two or-three pH units above the pH in the bulk solution. Although localized, these regions can nevertheless cause the chemical equilibrium in the solution undergoing electrodialysis to shift bicarbonate to carbonate ion, thus starting formation of calcium carbonate scale. This in turn facilitates precipitation of other scale forming materials such as e.g. calcium sulfate.

It has now been found that such scale formation in the electrodialysis step can be substantially reduced or avoided by introducing into the concentrate side of the electrodialysis unit an aqueous carrier in an amount such that precipitation of the ions present is substantially reduced or avoided.

SUMMARY OF THE INVENTION

The invention provides a process for the recovery of organic values from aqueous solutions containing both organic values and scale-forming ions, which process comprises in sequence introducing as feed an organic value-containing aqueous solution containing scale-forming ions to a membrane-containing electrodialysis zone to obtain: (1) a concentrate stream containing a major portion of the scale-forming ions from said feed, and (2) a diluate stream containing a major portion of the organic values in said feed, supplying to the concentrate side of the membranes within said electrodialysis zone an aqueous carrier stream substantially free of organic values and in an amount sufficient to substantially reduce or prevent the formation of scale on said membranes, withdrawing said concentrate stream from said electrodialysis zone, fractionating said diluate stream in a fractionation-distallation zone, to obtain: (1) at least one aqueous product stream containing a major portion of the water in said diluate stream, and (2) an enriched organic product stream containing a major portion of the organic values in said diluate stream, and withdrawing aid organic product stream from said fractionation distillation zone.

DESCRIPTION OF PREFERRED EMBODIMENTS

Electrodialysis is by now a well established industrial process. Basically, an electrodialysis unit comprises a plurality of membranes alternately anionic and cationic placed between an anode and a cathode connected to a direct current source. The membranes are usually separated from each other by 1 to 5 mm using appropriate spacers and the feed stream may be made to flow through a spacer creating a turbulent path in order to increase turbulence of the liquids contacting the membranes or in sheet type flow to reduce pumping pressure. The construction of the unit is generally in the form of a stack, like a filter stack. The membranes which usually contain ion exchange groups have a fixed positive or negative charge. The cationic membranes have negative fixed charges; the anionic membranes have positive fixed charges. Electrical neutrality in the membrane matrix is satisfied by the migrating cations (through cationic membranes) and anions, (through anionic exchange membranes).

If a feed is introduced uniformly from the top of the electrodialysis unit it would be found that the streams in the passages in the unit having an anion membrane on the cathode side of the passage and vice versa will become concentrate streams higher in ionized (herein electrolyte) components and the other streams in passages bounded by anion membranes on the anode side and cation membranes on the cathode side will become depleted in ionized components. Such depleted stream or streams are herein referred to as the diluate stream and will contain at least a majority of the organic values to be recovered.

Any material that is used for carrying out electrodialysis in practice is eligible as membrane material. A useful survey of such materials and of practical embodiments of electrodialysis units is given in, e.g. "Industrial Processing with Membranes", edited by R. E. Lacey and S. Loeb, Wiley-Interscience, New York, 1972, pp.6–7. However, it is greatly preferred to use "tight -pore membranes" instead of more or less conventional materials.

The more or less conventional membranes allow more water molecules to be transferred through the membrane per quantity of electric charge passed through than the tight-pore membranes. The phenomenon of simultaneous water transfer is called electroosmotic flux. Traditionally as this flux is lower, the concentrate will have a higher concentration, and when scale-forming ions are present, a higher propensity to form scale on the electrodialysis membranes.

In actual practice anion-selective membranes with an electroosmotic flux of from about 115 to 200 gram (water)/Faraday (electric charge transferred) (g/F) are called conventional membranes and anion-selective membranes with an electroosmotic flux of less than about 115 g/F are called membranes of the tight-pore type. For cation-selective membranes these values are somewhat-higher; those with a an electroosmotic flux of from about 210 to 300 g/F are called conventional membranes and so those with a value lower than about 210 g/F are called membranes of the tight-pore type. For many organic values to be recovered, such as e.g. polyhydric compounds, tight-pore membranes have the advantage of allowing easier passage to water than the organic compound, thus enhancing the retention of the organic in the diluate stream.

Usually the direct voltage applied between the anode and cathode advantageously lies in the range between 0 and 4.5 Volt, and is preferably in the range from about 0,5 to about 2.5 V. It is an advantage of the use of carrier water according to the invention the generally lower voltage may be applied when the carrier stream is applied. The separation by electrodialysis is advantageously accomplished with relatively little expenditure of electrical energy because concentration gradient against which the charged species migrate are much lower than in conventional electrodialysis processes. This modus operandi is also beneficial with respect to current densities, which can be kept far from their limiting values, at which polarization losses and extreme pH changes can occur locally.

Generally, for stability of the membranes, it is necessary to employ temperatures less than about 70° C. during electrodialysis. In terms of overall efficiency, it is preferred to carry out the electrodialysis step at temperatures in the range from about 20° to about 50° C.

The organic values recovered according to the invention will typically be present in the feed in amounts from about 1 to about 95% W, or more and preferably from about 2 to about 60% W. Generally the maximum allowable organic concentration will be determined by the viscosity of the feed solution at the operating temperature, which typically should be less than about 12 centipoise (cP), preferably less than about 10 cP, and most preferably less than 5 cP, which may be influenced by the configuration of the electrodialysis unit, e.g. sheet flow or tortuous path design and the number of parallel flow paths through the stack. The improvement according to the invention can be applied to any known separation by electrodialysis of organic compounds from electrolytes known to precipitate as scale. As organic values, the process is particularly suitable for recovering polyhydric organic compounds such as ethylene glycol, diethylene glycol, propane diol, butane diol, triethylene glycol, and glycerine. Exemplary processes are disclosed e.g. in U.S. Pat. Nos. 4,427,507; 4,599,178; and 4,640,754, all incorporated by reference.

The level of hardness ions i.e. of scale-forming components in the feed solution that may be present will depend somewhat on the particular species. For example, calcium, magnesium and barium sulfates can form scale, especially in the presence of bicarbonate ions. Iron and manganese can be tolerated only at very low levels, which level is somewhat interdependent upon the presence or absence of additional scale-forming ions. When iron and/or manganese are present in the feed, use of a commercially available "greensand" filter, a manganese-containing zeolitic filter, is recommended to pretreat the feed to safeguard agoinst precipitation of these ions on the membranes of the electrodialytic unit.

The amount of carrier water introduced into the concentrate side of the electrodialysis zone ordinarily will be influenced not only by the type and quantity of ions electrodialyzed from the feed solution, but in additin will be influenced by the quality of the carrier water as well. Generally scale formation may be avoided by maintaining the concentrations of the least soluble species in said concentrate side of the membranes in the electrodialysis unit at a level below about 75%, and preferably less than about 60% of the saturation level. Generally amounts of carrier water added to the concentrate side of the electrodialysis membranes will be of the order of 10 to 150%, and preferably from about 30 to about 100% by weight of the amount of organic value-containing feed to the electrodialysis unit.

As will be apparent to those skilled in the art, the water used as a carrier stream according to the invention, may be be subjected to separate pretreatment such as ion-exchange or even deionization to improve its quality and minimize the volume required. In a particularly preferred embodiment, at least one aqueous overhead fraction from fractional distillation of the diluate following electrodialysis is recycled as at least a portion of the aqueous carrier stream supplied to the concentrate side of the membranes within the electrodialysis zone. Such recycle stream may also be used to supply heat to the electrodialysis zone by controlling the condensation temperature of the overhead fraction.

The process according to the invention is particularly suitable for use in ,recovering organic polyhydric dehydrating materials used in drying $CO_2$ and/or natural gas. When these gases are produced from subterranean reservoirs, water which typically contains some dissolved salts such as chlorides, bicarbonates and sulfates of calcium, magnesium and sometimes barium, becomes entrained. The gas is then dried by absorption in a polyhydric organic compound such as diethylene glycol, glycerine, triethylene glycol and the like. It has been found that for recovery and regeneration of such organic sorbents, the water-laden spent solution often contains some crude petroleum which can foul or otherwise disrupt the electrodialysis step.

For processing spent dehydrating agent from drying of $CO_2$, it has been found that the spent material often contains considerable emulsified crude petroleum which should be removed prior to the electrodialysis step to minimize fouling of the electrodialysis membranes. Depending upon the "tightness" of the emulsion, conventional steps such as gravity separation i.e. "settling", passing through a filter/coalescer, changing the pH of the aqueous phase, e.g. acidification, or heating, may suffice to separate such petroleum oil. Alternately, extraction with a low density hydrocarbon fraction such as kerosene or No. 2 fuel oil has proven effective with more difficult emulsions. Often a guard bed of activated carbon installed to treat the feed to the electrodialysis unit has proved useful in protecting the membranes against fouling by minor amounts of entrained hydrocarbons in the feed. After separating the crude petroleum, the feed is introduced to the electrodialysis unit in conventional manner.

Another use of the improved process according to the invention is in recovering glycol from a typical waste stream found in an ethylene oxide plant. Particulars concerning the use of electrodialysis to recover glycols from such a stream may be found in U.S. Pat. No. 4,427,507, incorporated herein by reference.

Yet another option for the use of the present process relates to the recovery and re-use of butane-diol employed in a process for the preparation of $C_{10}$–$C_{20}$ alpha olefins by way of catalytic oligimerization of ethene. A description of this process for the preparation of olefins may be found in the article published by E. R. Freitas and C. R. Gum in Chemical Engineering Progress (January, 1979), pp.73–79.

The invention will now be illustrated by the following examples. The ionic concentrations in six samples of spent diethylene glycol hydrate inhibitor used for drying $CO_2$ was determined: results are shown in Table 1.

TABLE 1

Ionic Concentrations in Six DEG/$H_2O$ Hydrate Inhibitor Solutions in ppmw

| Samples | $Na^+$ | $Ca^{++}$ | $Mg^{++}$ | $Sr^{++}$ | $Fe^{++}$ | $Mn^{++}$ | $Cl^-$ | $SO_4$ | $HCO_3^-$ |
|---|---|---|---|---|---|---|---|---|---|
| A | 930 | 471 | 148 | 4.1 | 0.9 | 0.4 | 2540 | 73 | 147 |
| B | 629 | 449 | 156 | 2.8 | 4.8 | 0.6 | 2130 | 58 | 100 |
| C | 463 | 417 | 133 | 2.0 | 2.0 | 0.4 | 1810 | 40 | 95 |
| D | 378 | 284 | 124 | 2.2 | 0.4 | 2.6 | 1320 | 35 | 7 |
| E | 1090 | 485 | 160 | 4.8 | 0.2 | 0.6 | 2760 | 88 | 146 |
| F | 468 | 292 | 93 | 211 | 3.0 | 0.3 | 1490 | 48 | 80 |

As may be seem there is wide variation in the ionic content of such material

Experiments were carried out with diethylene glycol-water mixtures from drying $CO_2$ produced from subterranean sources. The electrodialysis unit used was the "Stack Pack" laboratory unit available from Ionics, Inc., however, modified to use only 10 cell pairs rather than the customary 20 cell pairs, in order to maximize exposure of the membranes to the feed solutions, thereby magnifying any problems such as scale formation and fouling. All experiments were carried out at 25° C. using tight pore membranes, namely cation exchange membrane (Ionics code number 61CZL386), and anion exchange membrane (code number 103QZL386). Run number 1 was run with spent hydrate inhibitor "as received"; runs 2 and 3 used the same starting solution however diluted with one part of water to three parts of inhibitor to determine the effects of varying concentration. In runs 1 and 2 an amount of carrier water equal to the feed rate was added to the concentrate stream in the electrodialysis unit; in run 3 the amount of carrier water was one-half the feed rate. Results are shown in Table 2.

TABLE 2

Desalinzation of Hydrate Inhibitor by ED with Carrier Water Added to Concentrate Side

| Runs | 1 | 2 | 3 |
|---|---|---|---|
| % w DEG | 36 | 27 | 27 |
| Current Efficiency | 91.7 | 95.5 | 92.1 |
| lbs NaCl removed/hr | 0.03 | 0.026 | 0.027 |
| Spec. Mem. Area $ft^2$/lb NaCl . Hr | 78.5 | 86.9 | 86.9 |
| Power, $Kwh^2$/lb NaCl | 0.267 | 0.26 | 0.266 |
| $Cl^-$ in DEG in feed/in diluate | 1783/226 | 1385/69 | 1345/76 |
| $Ca^{++}$ in feed/in diluate | 485/77 | 368/34 | 382/29 |
| $Mg^{++}$ in feed/in diluate | 246/0 | 165/0 | 144/0 |
| Final ppmw | | | |
| $HCO_3^-$ concentrate | 147 | 169 | 146 |
| $SO_4^{-3}$ in concentrate | 105 | 84 | 153 |
| Ratio of feed rate/carrier water (Volume Ratio) | 1.0 | 1.0 | 2.0 |
| DEG Loss % | 1.4 | 1.4 | 1.0 |

The current efficiency obtained with the undiluted feed is 92% (run 1); that obtained with the diluted feed is 95% or 92% depending upon the volume of the concentrate (ion-receiving stream). The loss of organic values into the concentrate stream was 1.4% in runs 1 and 2 and 1.1% in run 3. No scaling of the membranes was observed with any of these runs.

What is claimed is:

1. A process for the recovery of organic values from aqueous solutions containing both organic values and scale-forming ions, which process comprises in sequence electrodialyzing as feed an organic value-containing aqueous solution containing scale-forming ions in a membrane-containing electrodialysis unit to obtain: (1) a concentrate stream containing a major portion of the scale-forming ions from said feed, and (2) a diluate stream containing a major portion of the organic values in said feed, supplying to the side of the membranes within said electrodialysis unit forming said concentrate stream an aqueous carrier stream substantially free of organic values, and in an amount sufficient to substantially reduce or prevent the formation of scale on said membranes, withdrawing said concentrate stream from said electrodialysis unit, fractionating said dilute stream by fractionation-distillation, to obtain: (1) at least one aqueous product stream containing a major portion of the water in said diluate stream as an overhead fraction, and (2) an enriched organic product stream containing a major portion of the organic values in said diluate stream, recycling said overhead fraction as at least a portion of said aqueous carrier stream supplied to said side of the membranes forming said concentrate stream within said electrodialysis unit, and withdrawing said organic product stream from said fractionation distillation step.

2. A process as in claim 1, wherein the amount of said aqueous carrier stream supplied to the side of the membranes forming said concentrate stream is from about 30 to about 100 percent by weight of the amount of organic value-containing feed to said electrodialysis zone.

3. A process as in claim 1, wherein the temperature within said electrodialysis zone is in the range from about 15° to about 60° C.

4. A process as in claim 1, wherein said feed is a calcium ion-containing solution originating from a process for drying $CO_2$ produced from subterranean sources.

5. A process as in claim 1, wherein said feed is a bicarbonate ion-containing water from a process for drying $CO_2$.

6. A process as in claim 1, wherein said feed is a sulfate-ion containing water from a process for drying natural gas.

7. A process as in claim 1, wherein said feed is a bicarbonate-ion containing waste water containing glycols formed by the hydrolysis of ethylene oxide.

8. A process as in claim 1, wherein said feed is a bicarbonate ion-containing butanediol originating from a process for the preparation of $C_{10}$–$C_{20}$ alpha-olefins by way of oligimerization of ethene using a catalyst dissolved in butane diol.

* * * * *

UNITED STATES PATENT AND TRADEMARK OFFICE
CERTIFICATE OF CORRECTION

PATENT NO. : 4,810,340

DATED : March 7, 1989

INVENTOR(S) : George C. Blytas and Zaida Diaz

It is certified that error appears in the above-identified patent and that said Letters Patent is hereby corrected as shown below:

On the title page delete:

"[30] Foreign Application Priority Data
Nov. 13, 1986 [GB] United Kingdom ..... 8627130."

Signed and Sealed this

Twenty-fourth Day of October, 1989

*Attest:*

DONALD J. QUIGG

*Attesting Officer*  *Commissioner of Patents and Trademarks*